United States Patent
Peltz et al.

(10) Patent No.: US 9,492,901 B2
(45) Date of Patent: Nov. 15, 2016

(54) OPTICAL MEASUREMENT OF FASTENER PRELOAD

(71) Applicant: The Boeing Company, Chicago, IL (US)

(72) Inventors: Leora Peltz, Pasadena, CA (US); Robert E. Grip, Rancho Palos Verdes, CA (US); John J. Brown, Costa Mesa, CA (US)

(73) Assignee: The Boeing Company, Chicago, IL (US)

( * ) Notice: Subject to any disclaimer, the term of this patent is extended or adjusted under 35 U.S.C. 154(b) by 238 days.

(21) Appl. No.: 14/157,313

(22) Filed: Jan. 16, 2014

(65) Prior Publication Data

US 2015/0198195 A1 Jul. 16, 2015

(51) Int. Cl.

| | |
|---|---|
| *F16B 31/02* | (2006.01) |
| *B23P 19/06* | (2006.01) |
| *G01N 21/952* | (2006.01) |
| *G01L 5/16* | (2006.01) |
| *G01L 5/24* | (2006.01) |
| *G01B 11/16* | (2006.01) |
| *G01L 1/24* | (2006.01) |
| *G01L 5/00* | (2006.01) |
| *G01M 11/08* | (2006.01) |

(52) U.S. Cl.
CPC .............. *B23P 19/065* (2013.01); *F16B 31/02* (2013.01); *G01B 11/18* (2013.01); *G01L 1/246* (2013.01); *G01L 5/0004* (2013.01); *G01L 5/166* (2013.01); *G01L 5/24* (2013.01); *G01N 21/952* (2013.01); *F16B 2031/022* (2013.01); *G01M 11/086* (2013.01); *Y10T 29/49766* (2015.01)

(58) Field of Classification Search
CPC .... F16B 31/02; F16B 31/025; F16B 1/0071; F16B 2031/022; G01L 5/24; G01L 5/105; G01L 5/243
USPC ........................................ 411/8, 13, 14, 82.5
See application file for complete search history.

(56) References Cited

U.S. PATENT DOCUMENTS

| | | | | |
|---|---|---|---|---|
| 2,600,029 | A * | 6/1952 | Stone .................... | F16B 31/025 338/2 |
| 3,224,316 | A * | 12/1965 | Grikscheit .............. | F16B 31/02 116/212 |
| 4,553,124 | A * | 11/1985 | Malicki ................. | F16B 31/025 338/2 |
| 5,044,204 | A * | 9/1991 | Leighton ................. | F16B 31/02 29/761 |
| 5,783,751 | A * | 7/1998 | Maw ..................... | G01L 5/0004 73/761 |
| 5,945,665 | A | 8/1999 | Hay | |
| 6,101,884 | A | 8/2000 | Haake | |

(Continued)

FOREIGN PATENT DOCUMENTS

| | | |
|---|---|---|
| DE | 102010055991 A1 | 6/2012 |
| EP | 2056086 A1 | 5/2009 |
| JP | 2005010064 A | 1/2005 |

OTHER PUBLICATIONS

Search Report for related European Application No. EP 14189467; report dated Jul. 15, 2016.

(Continued)

*Primary Examiner* — Roberta Delisle
(74) *Attorney, Agent, or Firm* — Miller, Matthias & Hull LLP (57) ABSTRACT

A fastener comprises a head, and a shank having an outer surface and an axially-extending channel in the outer surface. Optically transmissive, strain-sensitive fills the channel.

21 Claims, 7 Drawing Sheets

(56) References Cited

U.S. PATENT DOCUMENTS

| | | | | |
|---|---|---|---|---|
| 6,250,863 | B1* | 6/2001 | Kamentser | F16B 31/028 116/212 |
| 7,293,466 | B2* | 11/2007 | Ohta | F16B 31/02 257/417 |
| 7,412,898 | B1* | 8/2008 | Smith | G01L 5/24 73/761 |
| 7,441,462 | B2* | 10/2008 | Kibblewhite | F16B 31/02 73/761 |
| 7,720,324 | B2 | 5/2010 | Haase et al. | |
| 8,276,461 | B2 | 10/2012 | Zwygart | |
| 2008/0253858 | A1* | 10/2008 | Hsieh | F16B 31/02 411/14 |
| 2010/0054891 | A1* | 3/2010 | Nishida | F16B 31/02 411/9 |

OTHER PUBLICATIONS

Canadian Office Action for related Application No. 2,869,179; report dated Nov. 25, 2015.

* cited by examiner

OPTICAL MEASUREMENT OF FASTENER PRELOAD

BACKGROUND

A commercial aircraft may include thousands of threaded fasteners that clamp up different components. The threaded fasteners may be installed at specified torques.

However, a specified torque might not produce a specified preload (e.g., due to friction between the fastener and nut). To ensure that the specified preload is achieved, the fasteners are oversized and overtorqued.

Oversized fasteners are undesirable. For a commercial aircraft having thousands of fasteners, the use of oversized fasteners increases the weight of the aircraft and, therefore, increases fuel costs and other operating costs.

SUMMARY

According to an embodiment herein, a fastener comprises a head, and a shank having an outer surface and an axially-extending channel in the outer surface. Optically transmissive, strain-sensitive material fills the channel.

According to another embodiment herein, a method comprises installing a fastener including a shank having a channel filled with strain-sensitive optical material, terminating the fastener while measuring fastener preload, and stopping the fastener termination when the measured preload reaches a target value. Measuring the preload includes coupling light into an input of the filled channel, measuring frequency of light at an output of the channel, and determining the preload from the measured frequency.

These features and functions may be achieved independently in various embodiments or may be combined in other embodiments. Further details of the embodiments can be seen with reference to the following description and drawings.

DETAILED DESCRIPTION

A fastener includes a head and shank. A channel extends axially along an outer surface of the shank. Optically transmissive, strain-sensitive material fills the channel. As used herein, a "filled channel" refers to a channel that is filled with the optically transmissive, strain-sensitive material. The filled channel may function as a waveguide or a resonator. Strain of the shank may be determined by coupling light into an input of the filled channel. This will manifest as changes in resonance of the filled channel, or interference between reflections in the filled channel. The strain is determined from a change in frequency of the light at an output of the filled channel. Preload on the fastener may be determined from the strain.

The preload may be determined as the fastener is being installed. This accurate determination of preload during installation allows a specified preload to be achieved. Advantageously, the fastener does not have to be oversized and/or overtorqued to ensure that the specified preload has been achieved.

As will become apparent from the description that follows, the filled channel is not limited to any particular geometric form. Some geometric forms of the filled channel include a single straight portion, whereas other configurations are more complex and have multiple portions with different shapes. These geometric forms are designed specifically to measure different parameters.

Figure 1:
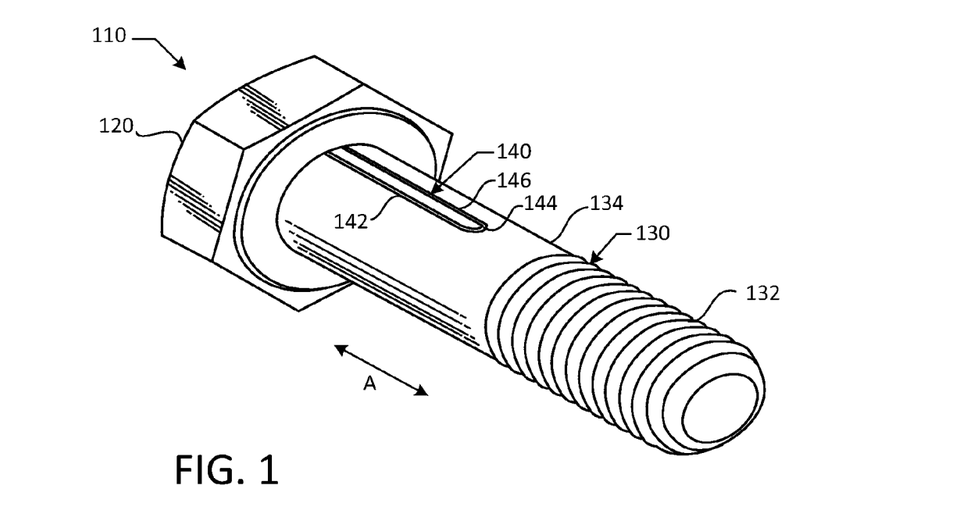
FIG. 1 is an illustration of a fastener including a shaft and a filled channel in an outer surface of the shaft.

Reference is made to FIG. 1, which illustrates a fastener 110 including a head 120, and a shank 130 having a threaded portion 132 and an unthreaded portion 134. The shank 130 extends from the head 120 in an axial direction (denoted by arrow A).

The fastener 110 further has a filled channel 140 in an outer surface of the unthreaded portion 134. The filled channel 140 of FIG. 1 has a U-shaped geometry. A first portion 142 of the filled channel 140 extends from the head 120 in a downward axial direction on the unthreaded portion 134 of the shank 130. A second portion 144 of the filled channel 140 extends circumferentially from the first portion 142. A third portion 146 of the filled channel 140 extends from the second portion 144 in the axial direction and terminates at the head 120. The width of the filled channel 140 in FIG. 1 is not to scale, but rather is exaggerated so as to be visible. In practice, each portion 142-146 of the filled channel 140 may have a width and depth of no more than 100 microns. The optically transmissive material filling these portions 142-146 may be homogeneous.

Figure 2:
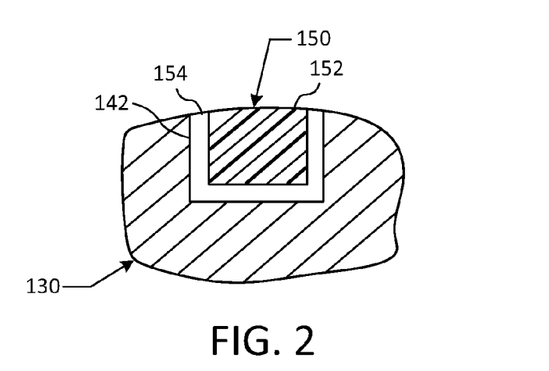
FIG. 2 is an illustration of a cross-section of a portion of the filled channel.

For now, consider the first portion 142 of the filled channel 140. A cross-section of the first portion 142 is illustrated in FIG. 2. Optically transmissive material 150 fills the first portion 142. The optically transmissive material 150 may include an optical core 152 and cladding 154 between the shank 130 and the optical core 152.

The materials in the optical core 152 and the cladding 154 have a difference in their index of refraction at the wavelength of the activation light. The index of refraction in the optical core 152 is larger than the index of refraction in the cladding 154. Examples for the core 152 and the cladding 154 include, but are not limited to, (1) silicone-type materials such as Dow Corning® OE-4140 for the optical core 152 and OE-4141 for the cladding 154; (2) siloxane polymer materials such as Dow Corning® OE-6636 for the core 152 and OE-6370 for the cladding 154; (3) acrylic/epoxies such as UV curable polymers for the core 152 and cladding 154; and (4) transparent fluoropolymers (e.g., CYTOP) for the cladding 154.

The optically transmissive material 150 is adhered to shank 130. For instance, the material for the optical core 152 is "flowed" into the channel 140, and adheres to the cladding 154 and/or shank 130.

Figure 3:
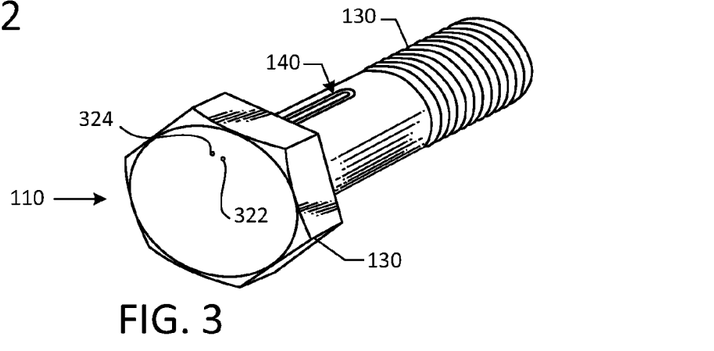
FIG. 3 is an illustration of a head of the fastener of FIG. 1.

Reference is made to FIG. 3. The fastener 110 may have input and output ports 322 and 324 located in the head 120. The ports 322 and 324 may be formed by drilling small openings in the head 120. These openings need not form a part of the channel 140, as they only allow access to the channel 140. (In other configurations, input and output ports may be located at the threaded end.)

Figure 4:
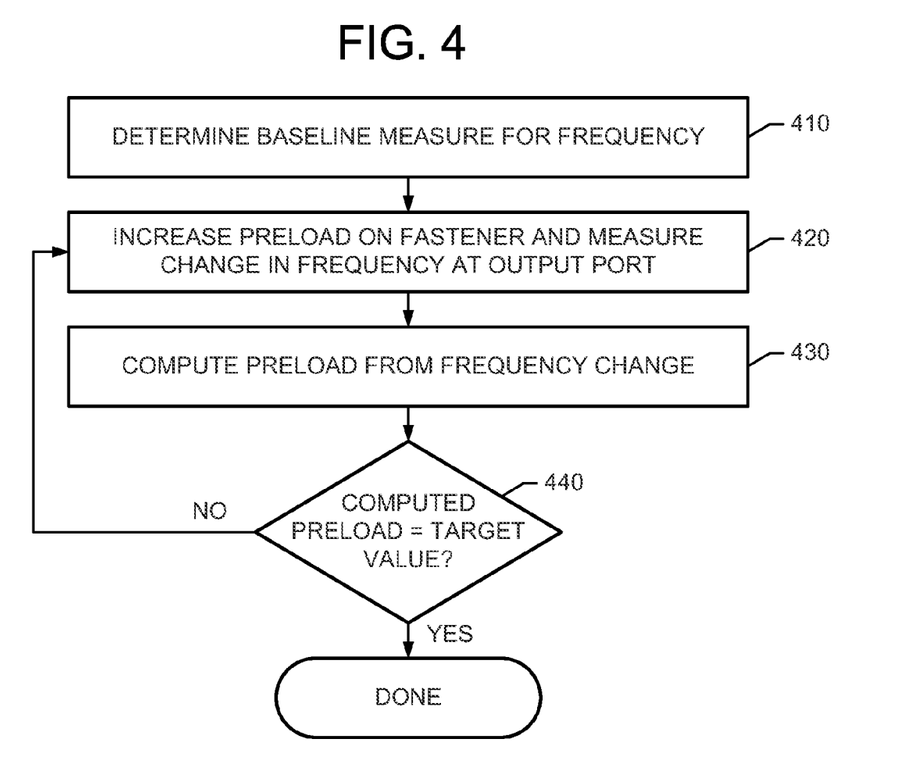
FIG. 4 is an illustration of a method of determining preload in the fastener of FIG. 1.

Reference is now made to FIG. 4. Preload on the fastener 110 may be determined as follows. At block 410, before a preload is applied to the fastener 110, input light is coupled into the input port 322, and received at the output port 324. Frequency of the light at the output port 324 is measured. This measurement will serve as a baseline measurement. Since the filled channel 140 functions as a waveguide, the interference between reflections in the filled channel 140 is measured.

At block 420, installation of the fastener 110 begins, as torque is applied to the fastener 110. For example, the fastener 110 is inserted in a stack of members and terminated with a nut. Torquing the nut onto the shank 130 places the shank 130 in tension and causes the shank 130 to deform in the axial direction (A). This strain translates into small mechanical deformation in the filled channel 140. This mechanical deformation changes the frequency of the light from the input port 322 to the output port 324.

As the torque is being applied, light is coupled into the input port 322. Frequency of light at the output port 324 is measured.

At block 430, strain is derived. A difference between the measured and the baseline frequencies is determined. Strain is derived from the frequency difference. A simple computation of axial stress in the shank 130 may be computed as the measured strain multiplied by the shank's modulus of elasticity. (A more complex computation may include additional terms, such as Poisson's ratio.) The preload on the fastener 110 may be computed as the product of the stress and the cross-sectional area of the shank 130.

At block 440, the computed preload is then compared to a target value. The functions at blocks 420 and 430 are repeated continuously until the measured preload reaches the target value.

The filled channel 140 provides higher accuracy and lower susceptibility to noise than a wire strain gauge. It also has a more precise radius of curvature. The filled channel 140 provides better coupling of strain than an optical wire extending through and glued to the central bore of a fastener.

In general, a filled channel at the surface of the shank can be configured with a wider variety of geometries than an optic fiber extending through the central bore of a fastener. Some of these geometries may also be used to determine fastener shear and/or bending.

Figure 5:
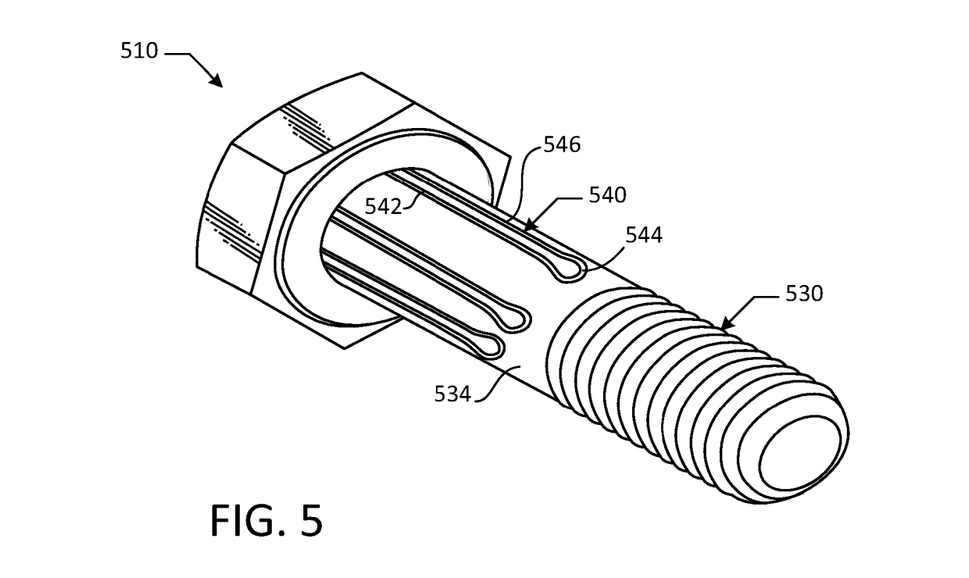
FIGS. 5-10 are illustrations of fasteners including filled channels having different geometries.
Figure 6:
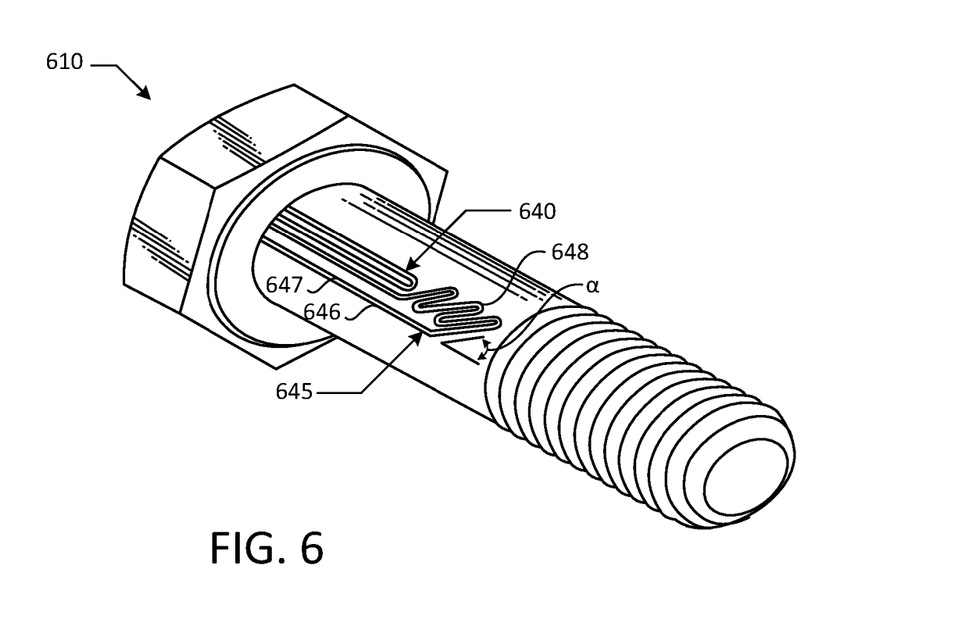

Reference is now made to FIG. 5, which illustrates a fastener 510 including a channel 540 having a first portion 542 that extends in a downward axial direction on the unthreaded portion 534 of the shank 530, a second portion 544 that is bulbous, and a third portion 546 that returns upward in the axial direction. The first and third portions 542 and 546, which extend in the axial direction, are constructed as coupling portions, which transmit light, but are less sensitive to deformations caused by strain Reference is now made to FIG. 6, which illustrates a fastener 610 including a first channel 640 for measuring axial strain, and a second channel 645 for measuring shear. The second channel 645 includes first and second axially-extending portions 646 and 647 which are constructed as coupling portions. In between these two portions 646 and 647 are one or more "fingers" 648 that extend at an angle ($\alpha$) relative to the axial direction. Shear forces may have both a transverse component and an axial component. To measure the resultant of these components rather than the individual components, the fingers 648 are oriented at the angle ($\alpha$). The optimal value for the angle ($\alpha$) corresponds to the expected relative magnitude of the components of the shear forces. For example, if the components are expected to be equal, the angle may be $\alpha=45$ degrees.

A fastener herein may have more than one of the same type of channel. Multiple channels of the same type may be used when the axial strain or shear is not distributed uniformly over the cross section of the shank. For instance, the fastener 510 of FIG. 5 includes multiple channels 540 for measuring bending that is not distributed uniformly across the cross-section of the shank 530.

Figure 7:
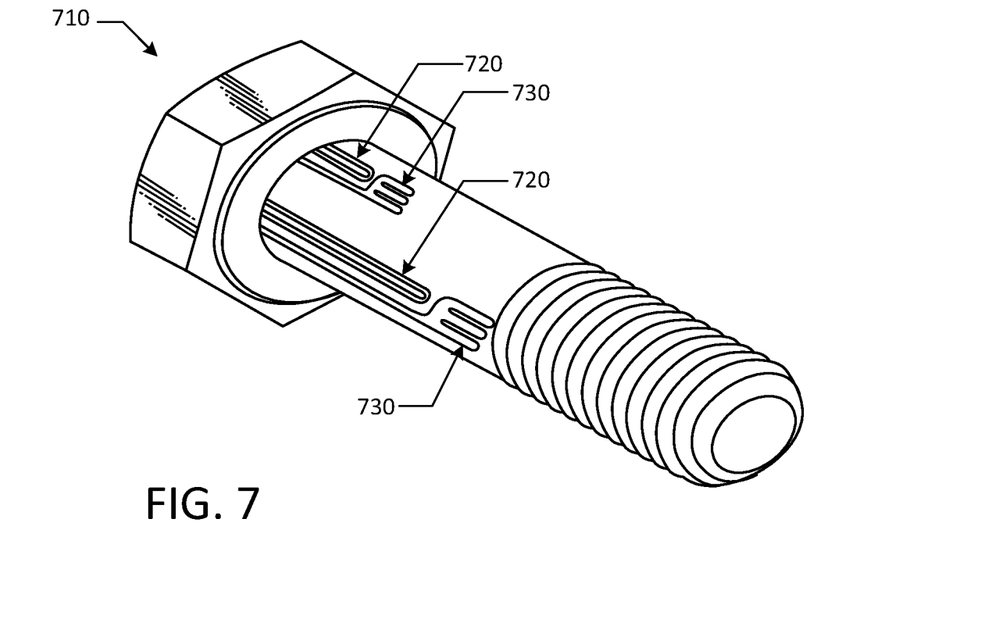

Reference is now made to FIG. 7, which illustrates a fastener 710 including multiple first channels 720 for measuring axial strain across the cross-section. The first channels 720 have different axial lengths for measuring axial strain at various locations along the axial dimension.

The fastener 710 also includes multiple second channels 730 for measuring shear across the cross-section. The coupling portions of the second channels 730 have different axial lengths for measuring shear at various locations along the axial dimension.

The use of multiple channels also enables reference calibration of the channels at load zero. All channels of the same type should provide identical measurements. Deviations among the measurements may indicate a non-conforming fastener.

Figure 8:
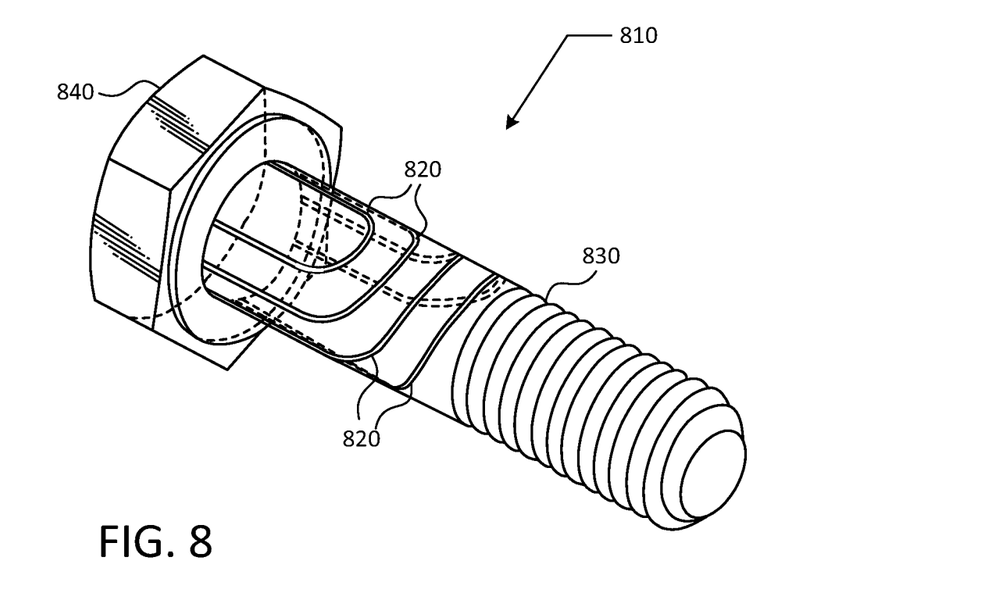
Figure 9:
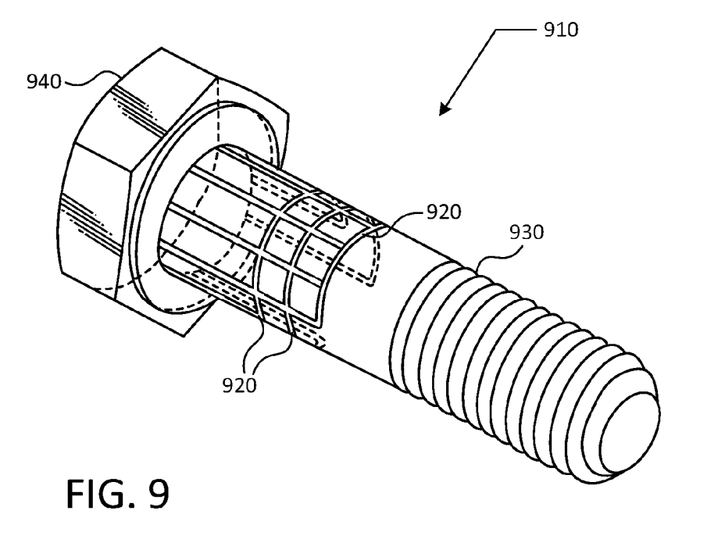

FIGS. 8 and 9 illustrate fasteners 810 and 910 having nested channels 820 and 920 for measuring axial strain. The channels 820 of FIG. 8 extend across different chords of the shank 830. Chord length increases with increasing distance from the fastener head 840. The channels 920 of FIG. 9 also extend across different chords of the shank 930. Chord length decreases with increasing distance from the fastener head 940.

Figure 10:
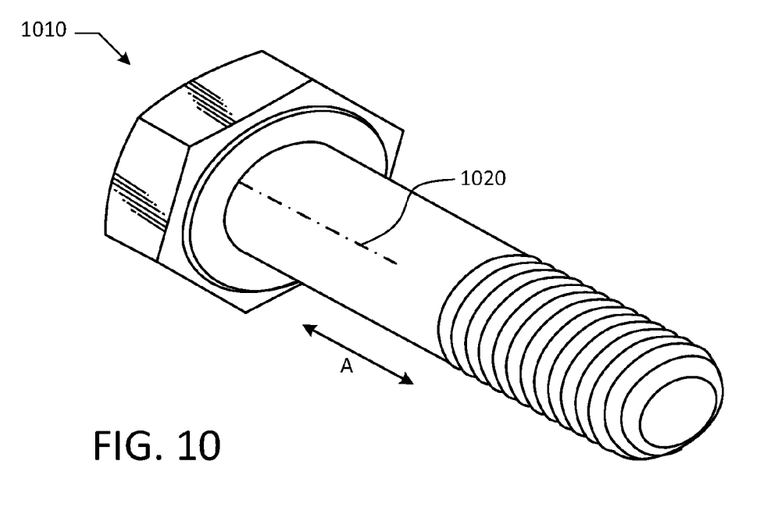

Reference is now made to FIG. 10, which illustrates a fastener 1010 including a channel 1020 having a single straight portion. Light is coupled into, and received at, a single port. The optical core in the channel 1020 has a graded refractive index such that the optically transmissive material functions as Bragg grating. The wavelength of light coupled into the optical material and reflected by the Bragg grating is substantially proportional to the distance between two variations of the refractive index of the optical material. Any variation of this distance resulting from strain may be detected by measuring the wavelength of the reflected light.

Figure 11:
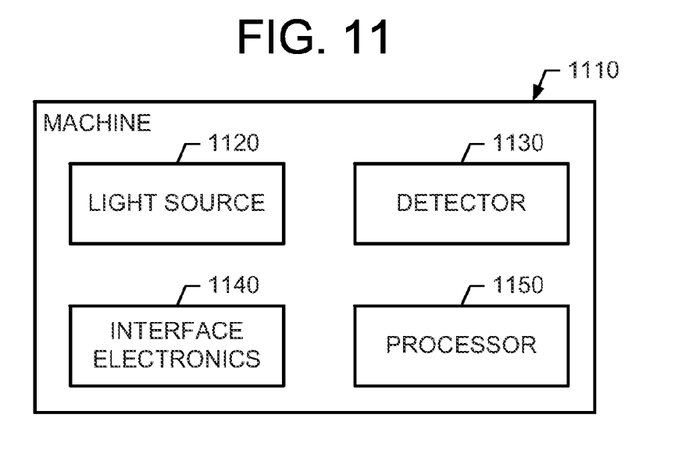
FIG. 11 is an illustration of a machine for determining preload on a fastener.

Reference is now made to FIG. 11, which illustrates a machine 1110 for determining preload on a fastener herein. The machine 1110 may be configured to couple an optical input signal into a filled channel and measure frequency of an output signal from the filled channel. The machine 1110 may be further configured to determine preload in the fastener's shank as a function of the measured frequency. For instance, the machine 1110 may include a light source 1120, detector 1130, and associated driver and interface electronics 1140 for coupling the input optical signal and measuring the frequency of the output optical signal. These components 1120-1140 may be miniaturized into a small electronics module, which may communicate with an onboard processor 1150 or a remote processor (e.g., health monitoring node, central computer, handheld readout instrument).

In some configurations, the machine 1110 may further include a torque wrench, which carries an electronics module. An onboard processor 1150 or a remote processor may determine the preload applied by the torque wrench.

In other configurations, the electronics module may be embedded in a sticker, which is attached to the head of a fastener over the input and output ports. The sticker receives power wirelessly and then wirelessly transmits the signals to a remote computing device.

In still other configurations, the machine 1110 includes a robot having an end effector for installing fasteners. The fasteners may be terminated manually or robotically. The end effector carries the electronics module, and an onboard processor 1150 or a remote processor determines the preload during fastener termination and stops the fastener termination when the preload equals a target value.

The robot may be configured to install fasteners in an aircraft. Some configurations of the robot may be used to determine preload during fastener installation. Some configurations may be used to determine preload after fastener installation. As an example of the latter, the preload may be determined during health monitoring of an aircraft.

Figure 12:
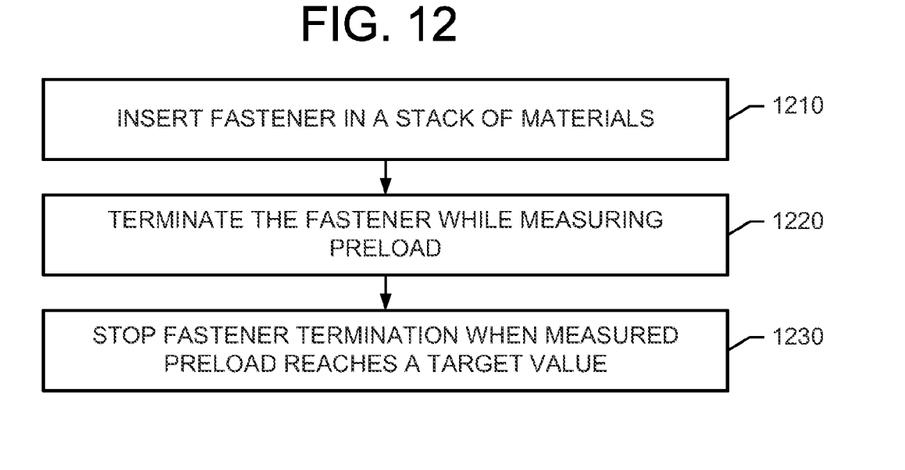
FIG. 12 is an illustration of a method of installing a fastener in an aircraft.

Reference is now made to FIG. 12, which illustrates a method of installing a fastener in an aircraft. At block 1210, a fastener is inserted in a stack of materials. As but one example, a hole is drilled in skin and an underlying stiffening substructure, and the fastener is inserted into the hole.

At block 1220, the fastener is terminated while measuring fastener preload. For example, a nut is threaded onto the threaded end of the fastener, and the nut is tightened to clamp up the stack. As the nut is being tightened, light is coupled into an input port of the filled channel, and frequency of light received at an output port of the filled channel is measured. The preload is determined from the measured frequency.

At block 1230, the fastener termination is stopped when the preload reaches a target value. Since the preload is determined at the end of fastener termination, the need for subsequent quality assurance to check torques on fasteners is eliminated.

Moreover, the assurance is more accurate, since preload is being measured instead of torque. Torque measurements can be affected by friction variation such as friction between the fastener and the nut.

The accurate measurement of preload during fastener installation enables a specified preload to be achieved during installation. Advantageously, the fastener does not have to be oversized and/or overtorqued to ensure that the specified preload has been achieved. Thus, fastener weight is reduced. The reduction in weight of a single fastener may seem trivial. However, given the large number of fasteners on an aircraft, the cumulative weight reduction can result in a substantial savings in fuel costs and other aircraft operating costs.

Figure 13:
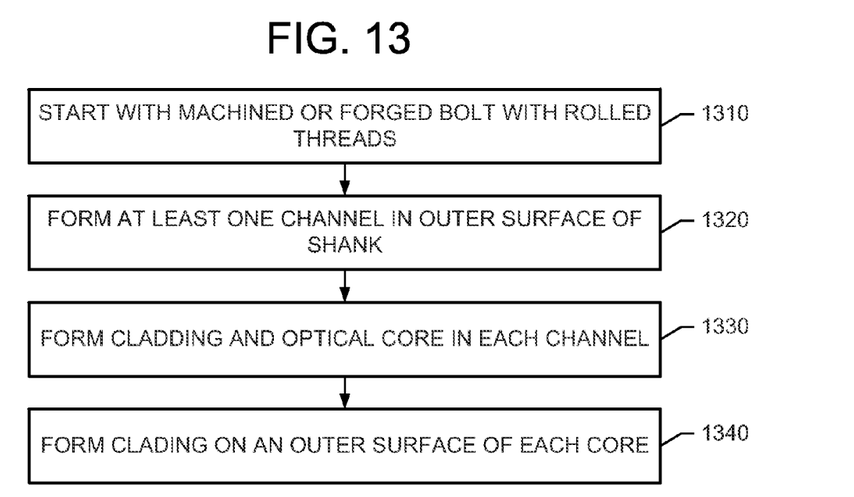
FIG. 13 is an illustration of a method of fabricating a fastener including a shaft, a channel in an outer surface of the shaft, and optical material in the channel.

Reference is now made to FIG. 13, which illustrates a method of manufacturing a fastener herein. The method starts with a machined or forged bolt with rolled threads (block 1310).

At block 1320, at least one channel is then formed in an outer surface of the fastener's shank (block 1320). Each channel may be formed, for example, by micro-machining, laser cut, or chemical etching.

At block 1330, optical material is formed in the channel. The cladding and the optical core may be formed by 3D printing, such as aerosol jet deposition.

At block 1340, additional cladding may be formed on an outer surface of the core. The additional cladding provides protection against mechanical damage.

The invention claimed is:

1. A fastener comprising:
   a head;
   a shank having an outer surface and an axially-extending channel in the outer surface; and
   optically transmissive, strain-sensitive material filling the channel, the optically transmissive, strain-sensitive material being adhered to the shank and including an optical core and cladding between the shank and the core.

2. The fastener of claim 1, wherein the shank includes a threaded portion and an unthreaded portion; and wherein the filled channel extends axially only on the unthreaded portion.

3. The fastener of claim 1, wherein the filled channel is less than 100 microns wide.

4. A method of installing the fastener of claim 1, comprising torquing the fastener while transmitting light to an input port of the filled channel, measuring frequency of light at an output port of the filled channel, and determining preload on the fastener as a function of the measured frequency.

5. The method of claim 4, further comprising torquing the fastener until the preload reaches a target value.

6. The fastener of claim 1, wherein the filled channel forms a waveguide.

7. The fastener of claim 1, wherein the filled channel is U-shaped to measure axial strain.

8. The fastener of claim 1, wherein the filled channel includes axially extending portions that are constructed as coupling portions, and at least one portion between the axially extending portions that is adhered to the shank.

9. The fastener of claim 1, wherein the filled channel includes a first axially-extending portion, a second bulbous portion, and a third axially-extending portion.

10. The fastener of claim 1, wherein the filled channel further includes an angled portion for measuring shear.

11. The fastener of claim 1, further comprising at least one additional filled channel in the outer surface of the shank, wherein the filled channels are spaced apart.

12. The fastener of claim 1, further comprising at least one additional filled channel in the outer surface of the shank, wherein the filled channels have different axial lengths.

13. The fastener of claim 1, wherein the filled channel includes an optical core having a graded refractive index such that the filled channel functions as Bragg grating.

14. A machine in combination with the fastener of claim 1, the machine comprising a light source for coupling an optical input signal into the filled channel; a detector for receiving an output signal from the channel; and a processor for determining preload in the shank as a function of an output of the detector.

15. A fastener comprising:
   a head;
   a shank having an outer surface and an axially-extending channel in the outer surface; and
   optically transmissive, strain-sensitive material filling the channel, the filled channel including axially extending portions that are constructed as coupling portions, and at least one portion between the axially extending portions that is adhered to the shank.

16. A fastener comprising:
   a head;
   a shank having an outer surface and an axially-extending channel in the outer surface; and
   optically transmissive, strain-sensitive material filling the channel, the filled channel further including an angled portion for measuring shear.

17. A fastener comprising:
   a head;
   a shank having an outer surface and an axially-extending channel in the outer surface; and optically transmissive, strain-sensitive material filling the channel, the optically transmissive, strain-sensitive material being adhered to the shank and including an optical core and cladding between the shank and the core, the optically transmissive material further including cladding on an outer surface of the core.

18. A fastener comprising:
a head;
a shank having an outer surface and an axially-extending channel in the outer surface;
optically transmissive, strain-sensitive material filling the channel; and
at least one additional filled channel in the outer surface of the shank, wherein the filled channels are spaced apart.

19. A fastener comprising:
a head;
a shank having an outer surface and an axially-extending channel in the outer surface;
optically transmissive, strain-sensitive material filling the channel; and
at least one additional filled channel in the outer surface of the shank, wherein the filled channels have different axial lengths.

20. A fastener comprising:
a head;
a shank having an outer surface and an axially-extending channel in the outer surface; and
optically transmissive, strain-sensitive material filling the channel, the filled channel including an optical core having a graded refractive index such that the filled channel functions as Bragg grating.

21. A fastener comprising:
a head;
a shank having an outer surface and an axially-extending channel in the outer surface;
optically-transmissive, strain-sensitive material filling the channel; and
a machine in combination with the fastener, the machine comprising a light source for coupling an optical input signal into the filled channel, a detector for receiving an output signal from the channel, and a processor for determining preload in the shank as a function of an output of the detector.

* * * * *